United States Patent [19]

Mackaness et al.

[11] 4,192,859

[45] Mar. 11, 1980

[54] CONTRAST MEDIA CONTAINING LIPOSOMES AS CARRIERS

[75] Inventors: George B. Mackaness, Princeton; Joseph P. Hou, Kendall Park, both of N.J.

[73] Assignee: E. R. Squibb & Sons, Inc., Princeton, N.J.

[21] Appl. No.: 946,976

[22] Filed: Sep. 29, 1978

[51] Int. Cl.$^2$ .............................................. A61K 29/02
[52] U.S. Cl. .......................................... 424/5; 424/4
[58] Field of Search ....................................... 424/4, 5

[56] References Cited

U.S. PATENT DOCUMENTS

| | | | |
|---|---|---|---|
| 2,613,172 | 10/1952 | Galler | 424/5 |
| 3,216,900 | 11/1965 | Embring | 424/4 |
| 3,356,575 | 12/1967 | Arbaeus et al. | 424/5 |
| 3,957,971 | 5/1976 | Oleniacz | 424/70 |

FOREIGN PATENT DOCUMENTS 3197M 3/1965 France .......................................... 424/4

OTHER PUBLICATIONS

*Clinical Pharmacology*, vol. 5, pp. 91–103, Pergamon Press, 1975.

*Primary Examiner*—Frederick E. Waddell
*Attorney, Agent, or Firm*—Lawrence S. Levinson; Burton Rodney

[57] ABSTRACT

X-Ray contrast media are provided containing an X-ray contrast agent such as N,N'-bis[2-hydroxy-1-(hydroxymethyl)ethyl]-5-[(2-hydroxy-1-oxopropyl)amino]-2,4,6-triiodo-1,3-benzenedicarboxamide, sodium diatrizoate, meglumine diatrizoate, sodium iodipamide, meglumine iodipamide and the like, and a liposome as a carrier therefor.

22 Claims, No Drawings

CONTRAST MEDIA CONTAINING LIPOSOMES AS CARRIERS

BACKGROUND OF THE INVENTION

X-Ray contrast media containing an X-ray contrast agent and a carrier therefor are used extensively in radiographic diagnostic techniques for the detection of cancer and other diseases. For example, in lymphography, lymphatic vessels and nodes can be visualized by either direct or indirect lymphographic techniques each of which requires the use of X-ray contrast media.

In direct lymphography, the contrast medium is directly injected into a lymphatic trunk or lymph node to provide visualization of the regional lymph structures proximal to the injection site and the lymphatic pathways draining that particular region, up to their entry into the venous system.

With respect to indirect lymphography, the contrast media is injected into the tissues where it enters many small lymph capillaries and is transported to the large lymphatic trunks and lymph nodes draining the injected tissue.

The contrast agents usually employed in lymphography may be of the water-soluble type, or water-insoluble, predominantly oily type preparations. Unfortunately, the radiologist has experienced persistent difficulties employing either type of contrast agent during both direct and indirect lymphographic techniques. For example, where water-soluble contrast agents such as N,N'-bis[2-hydroxy-1-(hydroxymethyl)ethyl]-5-[(2-hydroxy-1-oxopropyl)amino]-2,4,6-triiodo-1,3-benzenedicarboxamide (Bracco 15,000), sodium acetrizoate, meglumine acetrizoate, sodium diprotrizoate, meglumine diprotrizoate, iodamide meglumine, sodium diatrizoate, meglumine diatrizoate, and the like, are used, once injected, radiographs must be made almost immediately because of rapid diffusion of the contrast agent through the lymphatic walls and quick passage into the venous system. Thus, in many cases, the radiologist is unable to accomplish lymphatic diagnoses using water-soluble contrast agents.

Where a water-insoluble or oily contrast medium is used, such as ethiodized oil (Ethiodol) or Angiopaque (Thorotrast), because of the thick oily nature of the contrast medium, a pressure pump has to be used to give direct lymphatic cannulation. This is a difficult procedure for the radiologist. Moreover, use of the oily contrast medium is painful to the patient and is often associated with inflammation. In addition, the oily contrast medium remains at the injection site in contact with local tissue for a prolonged period thus tending to create toxicity problems.

Accordingly, it can be seen that in the field of lymphography, a great need still exists for contrast media which can be tolerated by the patient and yet remain for sufficient periods at the lymphatic sites to allow for proper examination and diagnoses.

Liposomes have been suggested as carriers for drugs; see Ryman, B. E., "The Use of Liposomes as Carriers of Drugs and Other Cell-Modifying Molecules," Proc. 6th Int'l. Congr. Pharmacol. 5, 91 (1976), published in "Drug Applications," *Clinicl Pharmacology*, Vol. 5, pp. 91-103, Pergamon Press (1975), Gregoriadis, G., "Enzyme or Drug Entrapment in Liposomes: Possible Biomedical Application," *Insolubilized Enzymes*, Ed. M. Salmona et al, Raven Press, N.T. 1974, pp. 165-177.

Liposomes are composed of lipid materials, predominantly of the phospholipid type. They are formed when phospholipids are allowed to swell in water or any aqueous salt solutions to form liquid crystals in the form of concentric bilayers with water entrapped between the lamellae (coarse liposomes). Upon suitable sonication the coarse liposomes form smaller similarly closed vesicles. "If water-soluble materials (such as X-ray contrast media) are included in the aqeos phase during the swelling of the lipids they become entrapped between the lipid bilayers. Alternatively, lipid soluble materials may be dissolved in the lipid and, hence, may be incorporated into the lipid bilayers themselves," Ryman, supra at p. 91.

Research has been conducted in the use of liposomes as carriers in enzyme replacement therapy. In addition, liposomes have been considered and tested for their suitability for entrapment of other substances of therapeutic interest including other proteins, and drugs such as 5-fluorouracil, methotrexate, actinomycin D, benzyl penicillin, colchicine, insulin, cyclic AMP and α-thiodeoxyguanosine, chelating agents, and cell modifying substances, such as hormones, antigens, and interferon inducers, Ryman, supra, p. 92. Ryman also indicates that consideration has been given to the entrapment of technetium (as $99mTcO_4^-$) in liposomes to carry out body monitoring. Ryman points out at p. 98 that "in an attempt to overcome the problem of rapid leaking of the technetium from the liposome we have entrapped albumin-bound technetium and have shown that with whole body scanning, the liver is very quickly visualised after injecting such liposomes into rats."

DESCRIPTION OF THE INVENTION

It has now been surprisingly found that liposomes make an excellent carrier for X-ray contrast agents, especially fo agents used in lymphography. Furthermore, it has been surprisingly and unexpectedly found that the use of liposomes as a carrier for X-ray contrast agents for use in lymphography substantially overcomes the aforementioned disadvantages associated with the use of water-soluble and oily contrast agents. Contrast media employing liposomes as carriers for contrast agents have been found to remain in lymphatic channels for sufficient periods to allow for adequate examination without discomfort and toxic reaction to the patient.

Thus, in accordance with the present invention, there is provided an X-ray contrast medium comprising an X-ray contrast agent and a liposome as a carrier therefor. The liposome includes cavities containing the contrast agent therein.

In addition, in accordance with the present invention, there are provided the above X-ray contrast medium especially for use in lymphographic techniques as well as in other radiographic techniques and a method for scanning lymphatic channels, and other body cavities and organs, employing such X-ray contrast medium.

The nature or characteristics of the contrast media of the inventio containing the liposome carrier will vary depending upon the composition of the lipid, the technique employed in preparing the liposome, and the nature of the contrast agent.

Examples of contrast agents suitable for use in the present invention include, but are not limited to the following: N,N'-bis[2-hydroxy-1-(hydroxymethyl)ethyl]-5-[(2-hydroxy-1-oxopropyl)-amino]-2,4,6-triiodo-1,3-benzenedicarboxamide (Bracco 15,000), metrizamide, diatrizoic acid, sodium diatrizoate, meglumine diatrizoate, acetrizoic acid and its soluble cationic salts, diprotrizoic acid and its soluble inorganic and organic cationic salts, iodamide, sodium iodipamide, meglumine iodipamide, iodohippuric acid and its soluble salts, iodomethamic acid and its soluble salts, iodopyraceti- iodo-2-pyridone-N-acetic acid and its soluble salts, 3,5-diiodo-4-pyridone-N-acetic acid (iodopyracet), 3,5-diiodo-4-pyridone-N-acetic acid diethanolamine salt, iodo-2-pyridone-N-acetic acid and its amine salts, iothalmic acid and its soluble salts, methanesulfonic acid, metrizoic acid and its soluble salts, sodium ipodate, ethiodized oil, iopanoic acid, iocetamic acid, tyropanoate sodium, iopydol, iophenoxic acid, iophendylate, and other chemically related iodinated contrast agents. Unless indicated otherwise, where applicable, the contrast agents which may be employed herein include inorganic, organic and cationic salts of the above contrast agent, such as the potassium salt, calcium salt, lithium salt, arginin salt, cystein salt, glycin salt, glycyl glycin salt, N-methyl glucosamine salt and other non-toxic aliphatic and alicyclic amines employed in preparing water-soluble salts.

The contrast agent will be present in the contrast media of the invention in an amount within the range of from about 20 to about 60% by weight of the contrast medium and preferably from about 30 to about 50% by weight of the contrast medium, depending upon the desired concentration of iodine.

The liposomes and preparations for same suitable for use herein include those disclosed in U.S. Pat. No. 3,957,971 to Oleniacz, G. Sessa et al, J. Lipid Res., Vol. 9, 310(1968), as well as in the various references discussed hereinbefore, and other liposomes known in the art.

Liposomes employed in the present invention generally comprise lipid materials, predominantly of the phospholipid type (for example, a sterol), lecithin, dicetyl phosphate, or stearylamine, in an organic solvent.

The liposomes may be prepared by mixing in a flask of suitable size desired amounts of lecithin, sterol with or without a charged component of phosphatidic acid, dicetyl phosphate or stearylamine in an organic solvent, such as chloroform, dichloromethane diethyl ether, carbon tetraoxide, ethyl acetate, dioxane, cyclohexane, and the like (chloroform being preferred). The organic solvent is evaporated under vacuum. The phospholipid formed in the flask is dispersed or hydrated by gentle shaking or stirring with a buffer solution of neutral pH containing a preweighed amount of contrast agent dissolved therein. The flask is shaken for two to six hours whereupon the lipids swell and form concentric lipid spherules (liposomes) with concomitant entrapment of water containing the contrast agent. Thus, a certain portion of the contrast agent is entrapped in liposome vehicles. The mixture is then sonicated briefly to decrease the size and viscosity of the liposomes.

The lecithin used herein may be commercial egg lecithin or may be derived from soybean oil.

Suitable sterols for use in the lipid mixture are cholesterol, phytosterol, sitosterol, sitosterol pyroglutamate, 7-dehydrocholesterol, lanosterol, and the like. It is also possible to use caprolactum.

The liposomes or lipid membranes preferably are binary mixtures of lecithin and cholesterol or ternary mixtures of lecithin, dicetyl phosphate, and a sterol selected from the group listed hereinabove, in the preferred molar ratios of 7:2:1, respectively. The molar percentage of lecithin may range from about 55 to about 85% and the sterol from about 15 to about 35% based on a binary mixture. The molar percentage of lecithin may range from about 50% to about 80%, the dicetyl phosphate from about 0 to about 30%, and the sterol from about 10% to about 30%, based on a ternary lipid mixture. Lecithin is employed to take advantage of its property of swelling in salt solutions. Dicetyl phosphate has the property of imparting a negative charge to the lipid membranes so that the mutual repulsive action of opposing channel surfaces widens the channels.

The components which constitute the lipid matrix are commercially available or may readily be prepared.

The pH consistency and viscosity of the final liposome preparations are controlled by the nature and amount of phospholipid used. The final liposome preparation is usually a homogeneous, viscous thick liquid brownish yellow in color and may have a typical egg lecithin or soybean oil smell depending upon the type of lecithin employed.

When applying a contrast medium containing a contrast agent and a liposome carrier therefor according to the invention, the contrast medium agent is administered to the body of the test object whereafter the body is exposed to X-rays and photographs may be taken or the image observed directly on a fluorescent screen, or other X-ray techniques may be applied in a conventional manner. The dose of contrast medium administered is selected according to the category of the investigation, so that a sufficient contrast effect is obtained.

The test object may include mammalian species, such as humans, dogs, cats, monkeys, sheep, pigs, horses, bovine animals and the like.

As indicated, the contrast medium of the invention is particularly suitable for use in lymphography. However, the contrast medium may be employed for visualizing many different body cavities and organs, such as the chest cavity including the brochial tree, and the gastrointestinal tract. In the latter instance, a single contrast agent or a mixture of two different typs of contrast agents, for example, meglumine diatrizoate and sodium ditrizoate is administered perorally as a thick liposomal formulation. The intestines can also be visibilized by administering the contrast medium rectally in the form of a liposomal enema. Another example is the visualization of blood vessels subsequent to the contrast medium being injected in the form of a sterile liposomal preparation. When injected intraveneously the contrast medium is excreted with the urine and enables visibilization of the renal pelvis, ureters and bladders. Further examples are the use of the contrast media in imaging the biliary system, hysterosalpingography, cholangiography, myelography, angiography, sialography, and silver and spleen imaging.

The following Examples represent preferred embodiments of the present invention.

EXAMPLE 1

A quantity of 1.4 g egg lecithin (egg phosphotidyl choline) and 0.6 g cholesterol are dissolved in 20 ml of chloroform. The chloroform is evaporated leaving a film of neutral phospholipid residue. Two grams of the phospholipid is then added to 7 ml of neutral buffered solution containing 4 g N,N'-bis[2-hydroxy-1-(hydroxymethyl)ethyl]-5-[(2-hydroxy-1-oxopropyl)amino]-2,4,6-triiodo-1,3-benzenedicarboxamide, (Bracco 15,000). The mixture is stirred with a magnetic stirrer until a final homogeneous liposomal mixture is obtained.

Ten milliliters of the final liposome preparation contains 4 g of the contrast agent and has a pH of 7.05 and a viscosity of 182 cp.

EXAMPLE 2

Two grams of neutral phospholipid residue, prepared as described in Example 1, is added to 6.7 ml of neutral buffered solution containing 4 g of sodium diatrizoate. The mixture is stirred with a magnetic stirrer until a homogeneous liposomal mixture is obtained. Ten milliliters of the final liposome preparation contains 4 g of sodium diatrizoate and has a pH of 7.03 and a viscosity of Ca. 2000 cp.

EXAMPLE 3

Two grams of neutral phospholipid residue, prepared as described in Example 1, is added to 6 ml of neutral buffered solution containing 4 g of meglumine diatrizoate. The mixture is stirred with a magnetic stirrer until a homogeneous liposomal mixture is obtained. Ten milliliters of the final liposome preparation contains 4 g of meglumine diatrizoate and has a pH of 7.05 and a viscosity of 700 cp.

EXAMPLE 4

A quantity of 1.26 g of egg lecithin (egg phosphotidyl choline), 0.54 g cholesterol and a 0.2 g dicetyl phosphate are dissolved in 20 ml of chloroform. The chloroform is evaporated leaving a film of negatively charged phospholipid residue. Two grams of the negatively charged phospholipid is then added to 7 ml of neutral buffered solution containing 5 g N,N'-bis[2-hydroxy-1-(hydroxymethyl)ethyl]-5-[(2-hydroxy-1-oxopropyl)amino]-2,4,6-triiodo-1,3-benzenedicarboxamide (Bracco 15,000). The mixture is stirred with a magnetic stirrer until a final homogeneous liposomal mixture is obtained. Ten milliliters of the final liposome preparation contains 5 g of the contrast agent and has a pH of 6 and a viscosity of ca. 2000 cp. The liposome mixture is sonicated by a Sonic 300 Dismembrator (Artek Systems Corp., Farmingdale, N.Y.) at 5° C. for 10 minutes. The viscosity of the final mixture is changed to ca. 200 cp.

EXAMPLE 5

Two grams of negatively charged phospholipid prepared as in Example 4 above is added to 7.5 ml of neutral buffer solution containing 4 g N,N'-bis[2-hydroxy-1-(hydroxymethyl)ethyl]-5-[(2-hydroxy-1-oxopropyl)amino]-2,4,6-triiodo-1,3-benzenedicarboxamide (Bracco 15,000). The mixture is stirred with a magnetic stirrer until a final homogeneous liposomal mixture is obtained. Ten ml of the final liposomal preparation contains 4 g of the contrast agent and has a pH of about 6 and a viscosity of ca. 160 cp after sonication at 5° C. for 10 minutes.

Liposomes thus prepared are spherules variously ranging in size from ca. 1.0 to about 25 microns in diameter but with approximately 70% being 5 microns in diameter.

EXAMPLE 6

Two grams of negatively charged phospholipid residue prepared as described in Example 4, is added to 7.5 ml of neutral buffered solution containing 2 g of sodium diatrizoate. The mixture is stirred with a magnetic stirrer until a homogeneous liposomal mixture is obtained. Ten milliliters of the final liposome preparation contains 2 g of sodium diatrizoate and has a pH of 6.7 and a viscosity of 106 cp.

EXAMPLE 7

Two grams of negatively charged phospholipid residue prepared as described in Example 4, is added to 7 ml of neutral buffered solution containing 2 g of meglumine diatrizoate. The mixture is stirred with a magnetic stirrer until a homogeneous liposomal mixture is obtained. Ten milliliters of the final liposome preparation contains 2 g of sodium diatrizoate and has a pH of 6.5 and a viscosity of 288 cp.

EXAMPLE 8

Seven grams of egg lecithin (egg phosphotidyl choline), 3 g cholesterol and 1 g hexadecylamine are dissolved in 100 ml of chloroform. The chloroform is evaporated leaving a film of positively charged phospholipid residue. Two grams of the positively charged phospholipid is then added to 7 ml of neutral buffered solution containing 4 g N,N'-bis[2-hydroxy-1-(hydroxymethyl)ethyl]-5-[(2-hydroxy-1oxopropyl)amino]-2,4,6-triiodo-1,3-benzenedicarboxamide, (Bracco 15,000). The mixture is stirred with a magnetic stirrer until a final homogeneous liposomal mixture is obtained. Ten milliliters of the final liposome preparation contains 4 g of the contrast agent and has a pH of 8.2 and a viscosity of 178 cp.

EXAMPLE 9

Two grams of positively charged phospholipid residue prepared as described in Example 7, is added to 7 ml of neutral buffered solution containing 4 g of sodium diatrizoate. The mixture is stirred with a magnetic stirrer until a homogeneous liposomal mixture is obtained. Ten milliliters of the final liposome preparation contains 4 g of sodium diatrizoate and has a pH of 9.7 and a viscosity of 140 cp.

EXAMPLE 10

Two grams of positively charged phospholipid residue, prepared as described in Example 7, is added to 8 ml of neutral buffered solution containing 4 g of meglumine diatrizoate. The mixture is stirred with a magnetic stirrer until a homogeneous liposomal mixture is obtained. Ten milliliters of the final liposome preparation contains 4 g of meglumine diatrizoate and has a pH of 8.5 and and viscosity of 160 cp.

The liposomes containing contrast agents prepared as described in Examples 1 to 9 may be employed as lymphangiographic media as well as for scanning the spleen and liver.

The following Example is carried out to show use of the contrast medium as prepared in Example 4 as a lymphangiographic agent.

EXAMPLES 11 AND 12

A male beagle is anesthetized with sodium pentobarbital (30 mg/kg). Evans Blue dye (0.5%) is injected into the interdigital webs of the hind feet. Toes are alternately flexed and extended, and the soft tissue webs are massaged to promote uptake of the dye into the lymphatics. The dorsal surface of each leg is shaved, and a small incision is made along the superficial dorsal metatarsal vein. A lymphatic trunk is exposed by sharp and blunt dissection. A small incision is made in the lymphatic trunk using modified Vannas scissors, and a PE10 catheter is inserted and secured with a 04 silk ligature. A small amount of saline is injected into the catheter to test for correct entrance into the lymphatic. The animal is positioned for ventrodorsal pelvic radiography, and a control radiograph is taken. Over a 3 minute period, 2 ml of a 50% aqueous solution of N,N'-bis[2-hydroxy-1(hydroxymethyl)ethyl]-5-[(2-hydroxy-1-oxopropyl)amino]-2,4,6-triiodo-1,3-benzenedicarboxamide is injected into the right leg (Control A), and 2 ml of 50% N,N'-bis[2-hydroxy-1-(hydroxymethyl)ethyl]-5-[(2-hydroxy-1-oxopropyl)-amino]-2,4,6-triiodo-1,3-benzenedicarboxamide in liposomes containing 10% Neobee oil (propylene glycol dicaprylate) is injected into the left leg (Example 11). Radiographs are taken immediately and 0.5, 1, 1.5, 2, 3, and 4 hours after injection.

Using an identical technique, a second male beagle is prepared and given over a 7 minute period, 2 ml of a 40% solution of N,N'-bis[2-hydroxy-1-(hydroxymethyl)ethyl]-5-[(2-hydroxy-1-oxopropyl)amino]-2,4,6-triiodo-1,3-benzenedicarboxamide (Control B) in the right leg and 2 ml of 40% N,N'-bis[2-hydroxy-1-(hydroxymethyl)ethyl]-5-[(2-hydroxy-1-oxopropyl)amino]-2,4,6-triiodo-1,3-benzenedicarboxamide in liposomes containing 10% Neobee oil in the left leg (Example 12).

After injection of aqueous solutions of N,N'-bis[2-hydroxy-1-(hydroxymethyl)ethyl]-5-[(2-hydroxy-1-oxopropyl)amino]-2,4,6-triiodo-1,3-benzenedicarboxamide (Controls A and B), both dogs show comparable visualization of lymphatics only to the distal third of the femoral trunk. Visualization disappears after 1.5 hours. The 50% formulation in liposomes (Example 11) immediately migrates to popliteal lymph nodes and remains there, gradually fading but still faintly evident at 4 hours. The 40% formulation in liposomes (Example 12) immediately migrates high into the iliac region and very gradually fades. Four hours after injection, popliteal lymph nodes and saphenous trunk are still visible.

What is claimed is:

1. An X-ray contrast medium comprising an X-ray contrast agent and a liposome as a carrier therefor, said liposome comprising a lecithin and a sterol, said X-ray contrast agent being present in an amount within the range of from about 20 to about 60% by weight of said contrast medium.

2. The X-ray contrast medium as defined in claim 1 wherein said X-ray contrast agent is selected from the group consisting of N,N'-bis[2-hydroxy-1-(hydroxymethyl)ethyl]-5-[(2-hydroxy-1-oxopropyl)amino]-2,4,6-triiodo-1,3-benzenedicarboxamide, metrizamide, diatrizoic acid, sodium diatrizoate, meglumine diatrizoate, acetrizoic acid and its soluble cationic salts, meglumine iocarmate, sodium iodipamide meglumine iodipamide, iodamide, iodohippuric acid and its soluble salts, diprotrizoic acid and its salts, iodomethamic acid, 3,5-diiodo-4-pyridone-N-acetic acid (iodopyracet), 3,5-diiodo-4-pyridone-N-acetic acid diethanolamine salt, iodo-2-pyridone-N-acetic acid and its amine salts, ioglycamic acid, iothalamic acid and its soluble salts, methanesulfonic acid, metrizoic acid, sodium metrizoate, sodium ipodate, ethiodized oil, iocetamic acid, iopanoic acid, tyropanoate sodium, iopydol, iophenoxic acid, and iophendylate, and mixtures thereof.

3. The X-ray contrast medium as defined in claim 2 wherein said X-ray contrast agent is N,N'-bis[2-hydroxy-1-(hydroxymethyl)ethyl]-5-[(2-hydroxy-1-oxopropyl)amino]-2,4,6-triiodo-1,3-benzenedicarboxamide.

4. The X-ray contrast medium as defined in claim 2 wherein said X-ray contrast agent is sodium diatrizoate.

5. The X-ray contrast medium as defined in claim 2 wherein said X-ray contrast agent is meglumine diatrizoate.

6. The X-ray contrast medium as defined in claim 2 wherein said X-ray contrast agent is meglumine iodipamide.

7. The X-ray contrast medium as defined in claim 1 wherein said lecithin comprises egg or soy lecithin.

8. The X-ray contrast medium as defined in claim 7 wherein said sterol is selected from the group consisting of cholesterol, phytosterol, sitosterol, sitosterol pyroglutamate, 7-dehydrocholesterol, lanosterol and mixtures thereof.

9. The X-ray contrast medium as defined in claim 7 wherein said sterol is cholesterol.

10. The X-ray contrast medium as defined in claim 7 wherein said liposome further includes dicetyl phosphate.

11. The X-ray contrast medium as defined in claim 7 wherein said liposome further includes hexadecylamine.

12. A method for the X-ray visualization of body cavities and organs, which comprises administering to the body of the test object an effective contrast producing amount of an X-ray contrast medium as defined in claim 1.

13. The method as defined in claim 11 wherein the liver is visualized.

14. The method as defined in claim 11 wherein the spleen is visualized.

15. The method as defined in claim 11 wherein the gall bladder is visualized.

16. The method as defined in claim 11 wherein the spinal cord is visualized.

17. A method as defined in claim 11 wherein the X-ray contrast agent employed is N,N'-bis[2-hydroxy-1-(hydroxymethyl)ethyl]-5-[(2-hydroxy-1-oxopropyl)amino]-2,4,6-triiodo-1,3-benzenedicarboxamide.

18. The method for the X-ray visualization of lymphatic channels, which comprises administering to the body of the test object an effective contrast producing amount of an X-ray contrast medium as defined in claim 1.

19. A method as defined in claim 14 wherein the X-ray contrast agent is N,N'-bis-[2-hydroxy-1-(hydroxymethyl)ethyl]-5-[(2-hydroxy-1-oxopropyl)amino]-2,4,6-triiodo-1,3-benzenedicarboxamide.

20. A method for the radiographic examination of the gastrointestinal tract, which comprises administering to the body of the test object an effective contrast producing amount of an X-ray contrast medium as defined in claim 1.

21. The X-ray contrast medium as defined in claim 1 where in said liposome carrier, said lecithin is present in an amount of from about 50 to about 85% by weight and said sterol is present in an amount of from about 10 to about 35% by weight.

22. The X-ray contrast medium as defined in claim 21 wherein said liposome carrier further includes dicetyl phosphate present in an amount of from 0 to about 30% by weight of said liposome carrier.

* * * * *

UNITED STATES PATENT AND TRADEMARK OFFICE
CERTIFICATE OF CORRECTION

PATENT NO. : 4,192,859

DATED : March 11, 1980

INVENTOR(S) : George B. Mackaness et al.

It is certified that error appears in the above—identified patent and that said Letters Patent are hereby corrected as shown below:

```
Column 2, line 37, "fo" should read --for--.
Column 2, line 60, "inventio" should read --invention--.
Column 4, line 54, "silver" should read --liver--.
Column 6, line 22, "loxopropyl" should read --1-oxopropyl--.
Column 7, line 6, "1(hydroxymethyl)" should read
   --1-(hydroxymethyl)--.
```

*Signed and Sealed this*

*Tenth* Day of *June 1980*

[SEAL]

*Attest:*

SIDNEY A. DIAMOND

*Attesting Officer*  *Commissioner of Patents and Trademarks*

UNITED STATES PATENT AND TRADEMARK OFFICE
CERTIFICATE OF CORRECTION

PATENT NO. : 4,192,859
DATED : March 11, 1980
INVENTOR(S) : George B. Mackaness et al.

It is certified that error appears in the above—identified patent and that said Letters Patent is hereby corrected as shown below:

Column 8, lines 30-41, Claims 13 to 17, in the first line of each claim, "11" should read --12--.

Signed and Sealed this

Thirty-first Day of January 1984

[SEAL]

Attest:

GERALD J. MOSSINGHOFF

Attesting Officer    Commissioner of Patents and Trademarks